(12) United States Patent
Bonnet et al.

(10) Patent No.: US 11,099,118 B2
(45) Date of Patent: Aug. 24, 2021

(54) DEVICE AND METHOD FOR SORTING BIOLOGICAL ENTITIES

(71) Applicant: ECOLE POLYTECHNIQUE FEDERALE DE LAUSANNE (EPFL), Lausanne (CH)

(72) Inventors: Frank Bonnet, Préverenges (CH); Norbert Crot, Epalinges (CH); Francesco Mondada, Bussigny (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 16/763,247

(22) PCT Filed: Nov. 26, 2018

(86) PCT No.: PCT/IB2018/059284
§ 371 (c)(1),
(2) Date: May 12, 2020

(87) PCT Pub. No.: WO2019/102422
PCT Pub. Date: May 31, 2019

(65) Prior Publication Data
US 2021/0072142 A1 Mar. 11, 2021

(30) Foreign Application Priority Data
Nov. 27, 2017 (WO) .................. PCT/IB2017/057415

(51) Int. Cl.
*G01N 15/14* (2006.01)
*G01N 15/00* (2006.01)

(52) U.S. Cl.
CPC ..... *G01N 15/1459* (2013.01); *G01N 15/1404* (2013.01); *G01N 2015/0065* (2013.01); *G01N 2015/149* (2013.01)

(58) Field of Classification Search
CPC ....... G01N 15/1459; G01N 2015/0065; G01N 2015/149; G01N 15/14; G01N 15/1404
(Continued)

(56) References Cited

U.S. PATENT DOCUMENTS 4,279,345 A * 7/1981 Allred .................. B07C 5/36
209/3.2
5,180,065 A * 1/1993 Touge ................ G01N 15/1404
209/3.1
(Continued)

FOREIGN PATENT DOCUMENTS

EP 0700434 A1 3/1996

OTHER PUBLICATIONS

Furlong, E. E., Profitt, D., & Scott, M. P. (2001). Automated sorting of live transgenic embryos. Nature biotechnology, 19(2), 153-156.
(Continued)

*Primary Examiner* — Roy M Punnoose
(74) *Attorney, Agent, or Firm* — Andre Roland S.A.; Nikolaus Schibli (57) ABSTRACT

A device for sorting biological entities is disclosed. The device comprises a channel to canalize the biological entities and a selector having slots to accommodate said entities. Means for detecting and analysing an optical parameter of the biological entities is coupled with the selector. The selector can switch from a rest position to a sorting position, or at least two sorting positions, based on the detected and analysed optical parameter, so that biological entities can be sorted on the basis of their optical properties. The device is particularly intended for sorting egg cells, zygotes, embryos, or larvae of an insect, an amphibian or a fish such as *Xenopus laevis*, *C. elegans* or zebrafish *Danio rerio*.

18 Claims, 6 Drawing Sheets

(58) Field of Classification Search
USPC .......................................................... 356/338
See application file for complete search history.

(56) References Cited

U.S. PATENT DOCUMENTS

| | | | | |
|---|---|---|---|---|
| 5,914,262 | A * | 6/1999 | MacMichael | ............ C12Q 1/04 |
| | | | | 435/243 |
| 7,392,908 | B2 * | 7/2008 | Frazier | .............. B01L 3/502761 |
| | | | | 209/3.1 |
| 8,820,538 | B1 * | 9/2014 | Lin | ................... B01L 3/502784 |
| | | | | 209/552 |
| 9,470,617 | B2 * | 10/2016 | Durack | .................. G01N 15/14 |
| 2003/0170609 | A1 * | 9/2003 | Rigler | ..................... G01N 15/14 |
| | | | | 435/4 |
| 2006/0180517 | A1 * | 8/2006 | Frazier | .............. G01N 15/1459 |
| | | | | 209/579 |
| 2011/0020855 | A1 * | 1/2011 | Shinoda | ............. G01N 15/1484 |
| | | | | 435/29 |
| 2011/0030808 | A1 * | 2/2011 | Chiou | ................. F16K 99/0061 |
| | | | | 137/13 |
| 2012/0122084 | A1 * | 5/2012 | Wagner | .............. G01N 15/1427 |
| | | | | 435/6.1 |
| 2018/0334670 | A1 * | 11/2018 | Bharadwaj | ........ B01L 3/502761 |

OTHER PUBLICATIONS

Graf, S. F., Hötzel, S., Liebel, U., Stemmer, A., & Knapp, H. F. (2011). Journal of the Association for Laboratory.
International Seach Report dated Apr. 2, 2019 for Application No. PCT/IB2018/059284.
Written Opinion of the ISA dated Apr. 2, 2019 for Application No. PCT/IB2018/059284.

* cited by examiner

DEVICE AND METHOD FOR SORTING BIOLOGICAL ENTITIES

CROSS-REFERENCE TO RELATED APPLICATIONS

The present application is a United States national stage application of International patent application PCT/IB2018/059284 filed on Nov. 26, 2018 designating the United States, and claims foreign priority to International patent application PCT/IB2017/057415 that was filed on Nov. 27, 2017, the contents of both documents being herewith incorporated by reference in their entirety.

TECHNICAL FIELD

The present invention pertains the field of mechanics and laboratory devices. In particular, the present invention relates to an apparatus for use as a sorter for biological entities such as embryos or egg cells.

BACKGROUND ART

Over the last 30 years, several vertebrate and invertebrate animals have been identified and extensively studied as fundamental models to address important questions in genetics, developmental biology, drug discovery, toxicology, and biomedical research. Amongst those model animals, some species have been selected and preferred because of certain particular experimental advantages, for example in developmental biology: the genetic similarity between these species and mammals, the small size, fast development, cheap husbandry and their relevance for replacing mammals in animal testing make of these models an excellent choice in a large range of research scenarios. As a way of example, the *C. elegans* nematode, the fruit fly *Drosophila melanogaster*, the zebrafish *Danio rerio* and the African clawed frog *Xenopus laevis* are of particular interest.

*Xenopus laevis* is widely used, powerful model organism to study developmental biology. The reasons for its worldwide usage in research lie in the high degree of conservation of most essential cellular and molecular mechanisms, it is inexpensive, easily manipulated and large amounts of material can be readily obtained for a variety of experimental procedures. Further, *Xenopus* eggs are abundant and unusually large in comparison to mammalian counterparts, with a diameter of approximately 1.2-1.4 mm.

The zebrafish has become another of the most important model organisms for in vivo studies of vertebrates in biology, both in fundamental research and for biomedical applications. Crucially, the transparency of the embryos makes them amenable to deep in vivo imaging. Further reasons for the attractiveness of the model include the complete genome sequence and an ever-growing number of transgenic and mutant fish lines, allowing detailed in vivo studies of gene regulation and function. Notably, zebrafish models exist for a broad range of human diseases, for example cardiovascular diseases, cancer or movement disorders.

Because of the small egg size and the relatively easy maintenance of zebrafish farms, the eggs also offer high-throughput screening possibilities. Zebrafish can lay a lot of eggs, one female for instance can lay up to 200 eggs during mating. Parts of these eggs will not produce any larvae. The fact that the egg will or will not produce a larva is visible to the naked eye, as the one that will not produce larvae are opaque and the ones that will produce larvae are transparent.

However, the current bottleneck for high-throughput screening is an efficient sorting and dispensing process of individual organisms into single reservoirs such as wells of a multiwell plate. One of the main tasks for the people working with zebrafish in laboratories is to take care of their reproduction and egg sorting, because the eggs that will not produce larvae might contaminate the fertilized ones. This monotonous task as of today is performed manually and is very time-consuming, prone to errors and complicated due to the small dimensions of the eggs (~1 mm diameter).

Several attempts have been made to automate the singularization of zebrafish eggs or larvae into multi well plates. A possibility is to use a robotic pick and place approach for sorting eggs from a petri dish into well plates. One such system is the CellBot (Fully Automated Single Cell Handling Platformb), where a delta robot, capable of several cycles per second, is combined with a fully motorized inverted light microscope (iMic from Till Photonics, Germany). The robot and the microscope move above and beneath the sample platform, which is stationary. Because the petri dish and the well plate are never moved during the sorting process, this arrangement prevents sloshing of the sample liquid. The inverted light microscope scans the petri dish and checks for eggs, if one is found, this egg is removed by a pipette tool attached to the delta robot and placed into the well plate. Unfortunately, such a pick and place system is costly, rather slow, and uses a large portion of lab space.

Further options are the COPAS and BioSorter instruments (both from Union Biometrica, Holliston, Mass.), which are specially designed for sorting of large biological entities (up to 1500 µm). These systems are capable of singularizing zebrafish eggs into 96-well plates in about 2 min. However, these systems were designed for high throughput flow cytometry and are therefore equipped with costly optics, not really necessary for simply singularizing large entities into well plates. Additionally, both systems are not capable of checking the quality of the entities sorted, such as shape, specific features or damage.

Graf et al. (J Lab Autom. 2011 April; 16(2):105-11) reported the construction of an image-based fluidic sorting system for automated zebrafish egg sorting into multi well plates. The system is a sorting device for large biological entities, such as zebrafish eggs and larvae or *Xenopus* oocytes, and consists of two main units named CellSorter and WellPlateFeeder. The CellSorter is used to sort single entities such as zebrafish eggs or larvae from a suspension, whereas the WellPlateFeeder, embodied as a gantry robot, places the single entities into a well of a multiwell plate. The actions of the CellSorter and the WellPlateFeeder are synchronized to ensure correct feeding of entities into the well plate.

After introducing the egg suspension into the CellSorter, the suspension is continuously moved by using a sliding and static ring. The two rings define a circular fluidic channel for the egg suspension. The sliding ring is rotated by an electro motor and drags along the suspension buffer because of viscous drag forces. Additionally, a small friction force acts on the chorion of the egg. The sum of drag and friction forces results in rolling of the egg along the fluidic channel and past the cameras positioned to visualize a portion of the channel.

To remove a single egg from the CellSorter, buffer is redirected inside the channel and, by a gentle push, moves the egg to the WellPlateFeeder, or any other subsequent system such as a microinjection module. A vision system installed along the fluidic path consists of one or two cameras and a light emitting diode array for illumination.

Additionally, excitation and emission filters can be introduced for using fluorescence signals for the identification of fluorescently labelled entities. Despite its efficiency, this system is quite complicated in terms of manufacturing, comprises a plurality of tubing means hard to clean after use, and pinch valves located at the interface between the CellSorter the WellPlateFeeder can led to malfunctioning of the CellSorter due to a travelling pressure wave.

Despite the advancements in this field, there is still a need for a user-friendly, reliable, automatized and low cost system for sorting and/or dispensing large biological entities such as zebrafish or *Xenopus* egg cells, zygotes or larvae.

SUMMARY OF INVENTION

In view of the drawbacks of the prior art solutions concerning the manipulations of biological entities, the inventors conceived and created a new kind of device and system for the mechanical sorting of biological entities such as egg cells or larvae. In particular, by coupling means for detecting and analysing an optical parameter of the biological entity with a switching selector, said entities can be sorted with ease and precision without the need of complicated device configurations.

Accordingly, it is one object of the present invention to provide a device for mechanically sorting a solid biological entity, wherein the sorting is based on an optical parameter of said biological entity, said device comprising:
  a channel having a proximal end, a distal end and an elongated body therebetween, said proximal end being operatively connectable with a reservoir comprising said biological entity;
  means for detecting and analysing an optical parameter of said biological entity; and
  a selector operatively connected with the distal end of said channel and with said means for detecting and analysing an optical parameter, said selector being shaped to accommodate said biological entity, wherein the selector can switch from a rest position to a sorting position, and preferably at least two sorting positions, based on the detection and analysis of the said optical parameter of the biological entity.

In one embodiment, the device is adapted to sort a solid biological entity dispersed in a fluid medium.

In one embodiment, said biological entity is an egg cell, a zygote, an embryo, a grain, a pollen, an animal tissue or a portion thereof or a larva.

In one embodiment, the channel has a diameter comprised between 0.5 and 20 mm, such as for instance between 0.5 and 10 mm or between 0.5 and 5 mm.

In one embodiment, the egg cell, the zygote, the embryo or the larva is derived from an insect, an amphibian or a fish.

In one embodiment, the means for detecting and analysing an optical parameter of said biological entity comprises an optical sensor and a light source.

In one embodiment, the optical parameter of said biological entity comprises transparency, reflectance, contour, morphology, fluorescence or any combination of the foregoing.

In one embodiment, the selector is shaped as a gearwheel comprising a plurality of slots shaped to accommodate the biological entity.

In one embodiment, the device further comprises a receiving reservoir in correspondence to each sorting position of the selector.

In one embodiment, the means for detecting and analysing an optical parameter further comprise a computer device operatively connected to the selector, said computer device comprising a computer program comprising instructions to:
  analyse the detected optical parameter, optionally comparing said optical parameter with reference data; and
  switch the selector from a rest position to one of at least two sorting positions based on the analysis of the said optical parameter of the biological entity.

A further object of the present invention relates to a robotic system comprising the device as previously described, said system comprising a robotic element adapted to enable the distribution of the biological entity into a reservoir after a sorting process, such as analysis of an optical parameter of a biological entity and before the switch of the selector from a rest position to a sorting position.

DESCRIPTION OF EMBODIMENTS

The present invention will be clarified in the following by means of the following description of those embodiments of the present invention which are depicted in the drawings. It is however to be understood that the present invention is not limited to the embodiments described in the following and depicted in the drawings; to the contrary, the scope of the present invention is defined by the claims. Moreover, it is to be understood that the present invention is not limited to the specific conditions or parameters described and/or shown in the following, and that the terminology used herein is for the purpose of describing particular embodiments by way of example only and is not intended to be limiting of the invention as claimed.

As used herein and in the appended claims, the singular forms "a", "an" and "the" include plural referents unless the context clearly dictates otherwise. Also, the use of "or" means "and/or" unless stated otherwise. Similarly, "comprise", "comprises", "comprising", "include", "includes" and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

Figure 1:
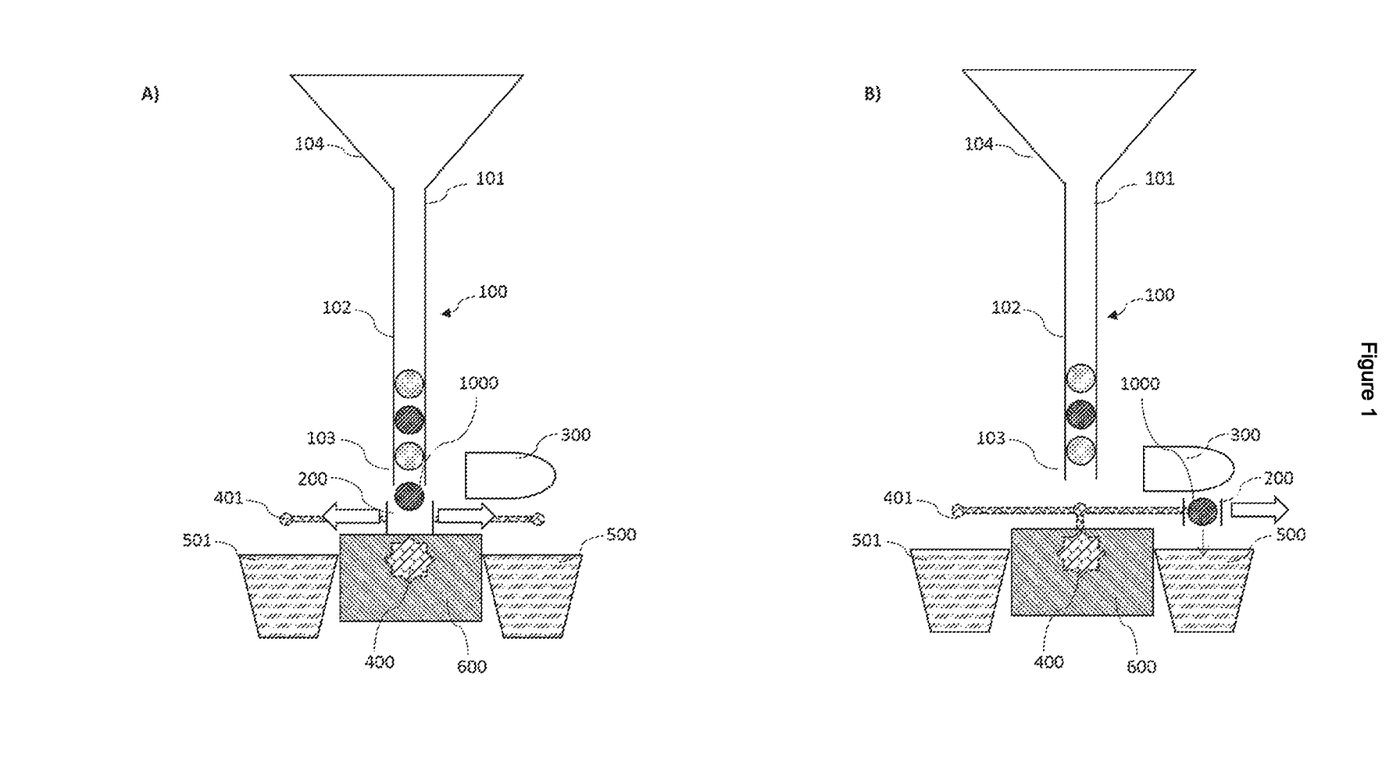
FIG. 1 shows one embodiment of the device of the present invention in operation, the device having a selector embodied as a chamber operatively connected with a motor actuator, said selector being in a rest position (1A) to accommodate a biological entity coming from an upper channel, and in a sorting position (1B) upon detection and analysis of an optical parameter of the biological entity.

With reference to FIG. 1, one embodiment of the device of the present invention is shown. The device comprises a channel 100 comprising a proximal end 101, a distal end 103 an elongated body 102 therebetween that is advantageously operatively connected or connectable with a reservoir 104, adapted to hold one or preferably a plurality of solid biological entities 1000, through said proximal end 101. The embodiment shown in FIG. 1 schematically depicts one configuration of the device of the invention; however, it is understood that deviations from this design can be contemplated, in which for instance more than one channel 100 or elements thereof (proximal end 101, distal end 103 and/or elongated body 102) can be present, to allow for instance multiplexed analyses to be run in parallel, without departing from the general inventive concept and scope of the invention. Moreover, reservoir 104 does not form part of the disclosed device, and his shown in the present embodiment for clarity purposes only.

For the sake of clarity, in the frame of the present disclosure, the expression "operatively connected" as well as "operatively connectable" reflects a functional relationship between the several components of the device of the invention between them, that is, the term means that the components are correlated in a way as to perform a designated function. The "designated function" can change depending on the different components involved in the connection; for instance, the designated function of a reservoir 104 operatively connected or connectable with a channel 100 is that to allow the loading of a biological entity from the reservoir 104 into the channel 100. A person skilled in the art would easily understand and figure out what are the designated functions of each and every component of the system of the invention, as well as their correlations, on the basis of the present disclosure.

In one embodiment, a pressure source is operatively connected with channel 100, reservoir 104 or both in a way as to generate a driving pressure thereon in order to let the biological entity 1000 flow throughout the channel 100. The pressure applied can be a positive pressure, i.e. when the applied pressure increases the internal reservoir 104 and/or channel 100 fluid pressure, or a negative pressure, i.e. when the applied pressure diminishes the internal reservoir 104 and/or channel 100 fluid pressure, as in case of a suction. Suitable means of altering the pressure within the device are external or integrated pumps or micropumps, combinations of capillary forces and electrokinetic mechanisms, a syringe or simply hydrostatic pressure. In this latter case, no pressure sources are necessarily needed if the entire device is located underwater, as will be detailed later on in one embodiment of the invention.

Once loaded into channel 100 through its proximal end 101, a biological entity 1000 is allowed to flow throughout the body 102 up to the distal end 103 of the channel where a selector 200 is placed. At any point along the body 102 of the channel 100, and preferably at its distal end 103, means 300 for detecting and analysing an optical parameter of said biological entity 1000 is located. In particular, said means 300 comprise an optical sensor and a light source adapted to reveal an optical parameter of the biological entity 1000 such as transparency or opacity, reflectance, contour, morphology, fluorescence or any combination of the foregoing. For instance, a light source can be arranged to illuminate a portion of the channel 100, such as its body 102 or its distal end 103, where a biological entity 1000 is flowed, and a light detection means can be arranged to capture the light scattered, absorbed or reflected by the said biological entity 1000. In this embodiment of the system of the invention, any light source can be used to illuminate the channel 100 of the device; these include, but are not limited to, white light, fluorescent light, infrared light, UV light, laser light, LED light and even sunlight. A simple embodiment of the system of the invention relies in the device as disclosed coupled with a camera as a detection means for e.g. assessing the morphology or the contour of the biological entity 1000: in this alternative, even the sunlight can be a suitable illumination means. Another simple alternative is the coupling of a LED light source with a photodiode sensor for e.g. assessing the transparency/opacity of the biological entity 1000. As it will be evident, in the described embodiment, at least the portion of the channel 100 where the biological entity 1000 is illuminated by means 300 is substantially made of a transparent material, such as transparent polymeric plastics or glass. However, as it will be described in more details later on, means 300 for detecting and analysing an optical parameter of a biological entity 1000 can be located elsewhere, such as for instance in correspondence of the selector 200.

As anticipated, a selector 200 is operatively connected with the distal end 103 of the channel 100 and with said means 300 for detecting and analysing an optical parameter. The selector 200 is designed to accommodate a biological entity 1000, preferably one at a time, and is operated so that it can switch from a rest position to a sorting position, preferably at least two sorting positions, based on the detection and analysis of the said optical parameter of the biological entity 1000. In some embodiments, the selector 200 is operatively connected with a motor actuator 400 such as a rotational actuator or a linear actuator that permits the displacement of the selector 200 from a first rest position A to at least a second and third switch position A' and A". Rest position A corresponds to the position in which the selector 200 is located in correspondence of the exit point of the distal end 103 of the channel 100, so to accommodate a biological entity 1000 flowing therefrom. At that time, means 300 for detecting and analysing an optical parameter of said biological entity 1000 detects and elaborates one or a plurality of optical parameters so to assign a value to it (them), and to therefore operate the motor actuator 400 in order to displace said selector 200 into a second or third switching positions A' or A". As a way of example, transparency/opacity of a biological entity 1000 is firstly detected and then elaborated by means 300 in order to assign a transparency value to the biological entity under examination. A "transparency threshold" is set for biological entities 1000, in a way that, if said threshold is not reached, means 300 will operate the motor actuator 400 so to displace the selector 200 in a second position A', whereas it the threshold is reached or exceeded, means 300 will operate the motor actuator 400 so to displace the selector 200 in a third position A".

In some preferred embodiments, means for detecting and analysing an optical parameter 300 further comprise a computer device operatively connected to the selector 200, said computer device comprising a computer program comprising instructions to:

analyse the detected optical parameter, optionally comparing said optical parameter with reference data; and
switch the selector 200 from a rest position to a sorting position, or one of at least two sorting positions A' or A", based on the analysis of the said optical parameter of the biological entity 1000.

In the embodiment shown in FIG. 1, the device further comprises a support 600 adapted to host the motor actuator 400 and/or to act as the floor of the selector 200, that is fabricated in this embodiment as a small container made of a continuous wall and with top and bottom openings. The motor actuator 400 is coupled with a two-arms selector support 401 that allows the selector 200 to slide along a longitudinal direction on two sorting positions A' or A", in the drawing located on the left and on the right with regard to the rest position A. In an alternative embodiment, sorting positions A' or A" can be located in non-opposed direction, but at two different locations along the same sorting direction. In this embodiment, a single arm selector support having two sorting positions would suffice. A single movable arm could however also be used in the context of opposed (e.g. left and right) sorting positions. Moreover, it is understood that more than two sorting positions of the selector 200 are envisageable in the frame of the invention, for example when a plurality of optical parameters or thresholds thereof are assessed.

Figure 2:
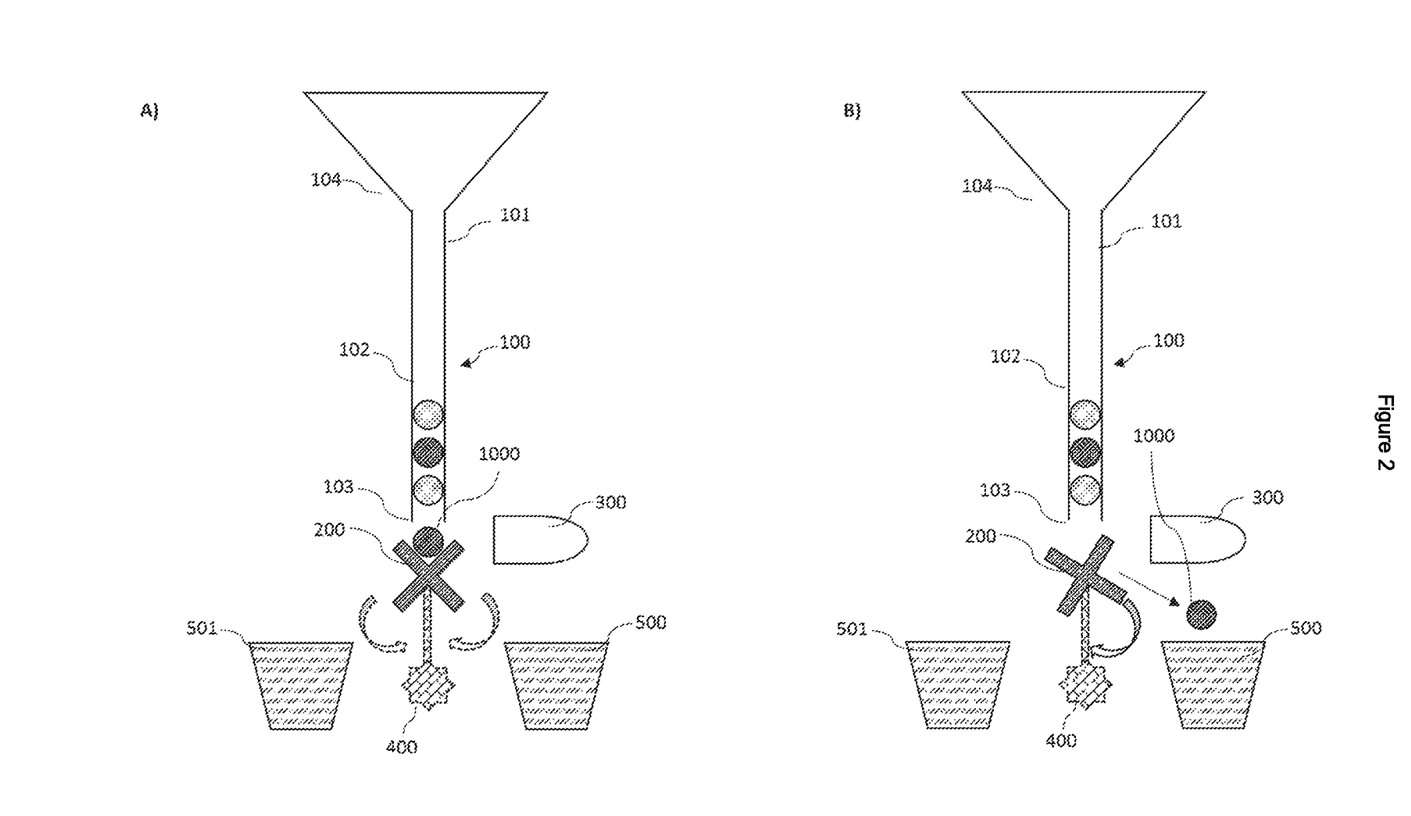
FIG. 2 depicts another embodiment of the device of the present invention in operation, both in a rest position (2A) or sorting position (2B), wherein the selector is embodied as a gearwheel having a plurality of slots to accommodate a biological entity.

In an alternative embodiment shown in FIG. 2, the selector 200 is embodied as a gearwheel comprising a plurality of slots adapted to accommodate the biological entity 1000. In this case, motor actuator 400 is preferably a rotational actuator that can operate a clockwise or counter-clockwise rotation of the selector 200 to allow the dispensing of the biological entity 1000. In the depicted embodiments, the biological entity 1000 is released upon sorting on receiving reservoirs 500 or 501, which in one embodiment can be included in the device, advantageously located in correspondence to each of the sorting positions of the selector 200 such as a second and third sorting positions A' or A".

The device of the invention has been specially conceived and constructed to sort biological entities of interest for research purposes. In this context, preferred biological entities according to the needs and goals of the invented device are egg cells, zygotes, embryos, animal tissues or a portion thereof or larvae. However, the device is suitably adaptable to work with grains, seed or pollens. Particularly, preferred egg cells, zygotes, embryos or larvae are those derived from an insect, an amphibian or a fish such as zebrafish *Danio rerio, C. elegans, Drosophila melanogaster*, or *Xenopus laevis*. Nonetheless, egg cells, zygotes or embryos of mammals such as mice, rats or primates can be sorted depending on the need or circumstances.

Since biological entities are typically dispersed in a fluid medium such as culture media or physiological fluids, in some embodiments the device is adapted to sort a solid biological entity dispersed in a fluid medium. To this aim, the elements of the device are shaped and manufactured in such a way that biological entities can flow together with the dispersing medium, and the materials used shall allow the facile flow of suspended entities without any major fluidic constraint. In particular, the channel 100 in which the biological entities are loaded and flowed should have a size and a shape customized to operate in a classic, normal fluidic regime; said channel has a diameter comprised typically between 0.5 and 20 mm, such as between 0.5 and 10 mm or between 0.5 and 5 mm, which is a range typically fitting with the size of the biological entities of interest.

Furthermore, in some embodiments, the device is adapted to work underwater, i.e. it is substantially made of materials compatible with underwater operations and/or is manufactured to facilitate underwater operations. For instance, means 300 or portions thereof, selector 200 and/or the actuator 400, as well as any connected or connectable parts, are conceived and manufactured to work in underwater environments or conditions; as a way of example, supporting structures can be made of solid materials such as solid plastics, glass or metals to allow the placement of the device into e.g. the bottom of a fish tank, and/or means 300 as well actuator 400 can be encapsulated to avoid water-related functional damages. These aspects of the invented device facilitate the sorting operations of biological entities such as zebrafish eggs or larvae, which are typically released and grown in water and at the same time sink.

In one embodiment, the device according to the invention can be coupled with a robotic element adapted to enable the distribution of the biological entities into a reservoir after the sorting process so to form a robotic system. To this aim, a robotic element can be for instance a movable platform adapted to accommodate a multi-well plate, said platform moving according to the sorting process so to have e.g. one biological entity dispensed for each well of a multi-well plate. In the frame of a robotic system, a device having a single sorting position of the selector 200 could be sufficient for an efficient sorting process: the selector can switch from a rest position to the sorting position upon detection of an optical parameter of the biological entity, and the samples can be disposed or chosen due to the movement of the moving platform, rationally selecting the receiving reservoir for any analysed biological entity.

Figure 3:
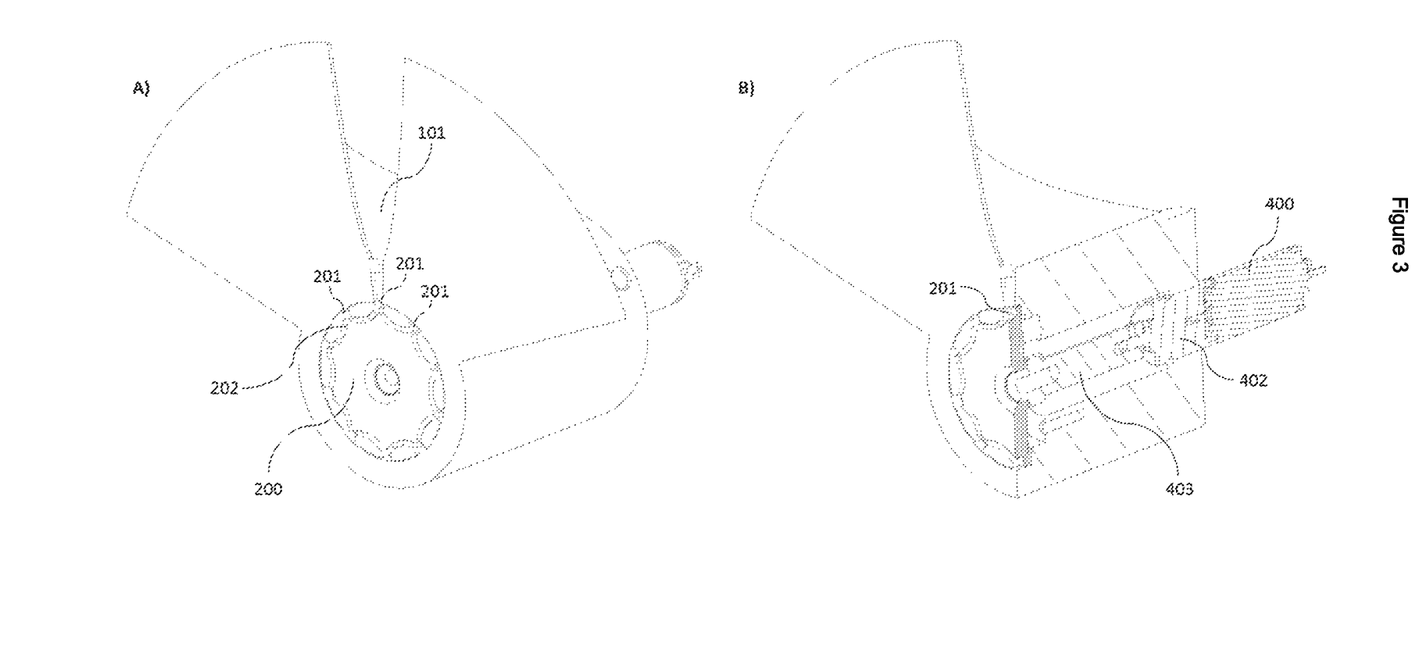
FIG. 3A shows an isometric view of an implemented embodiment of the device's selecting portion according to the invention.
FIG. 3B depicts a cross-sectional view of the same embodiment.
Figure 4:
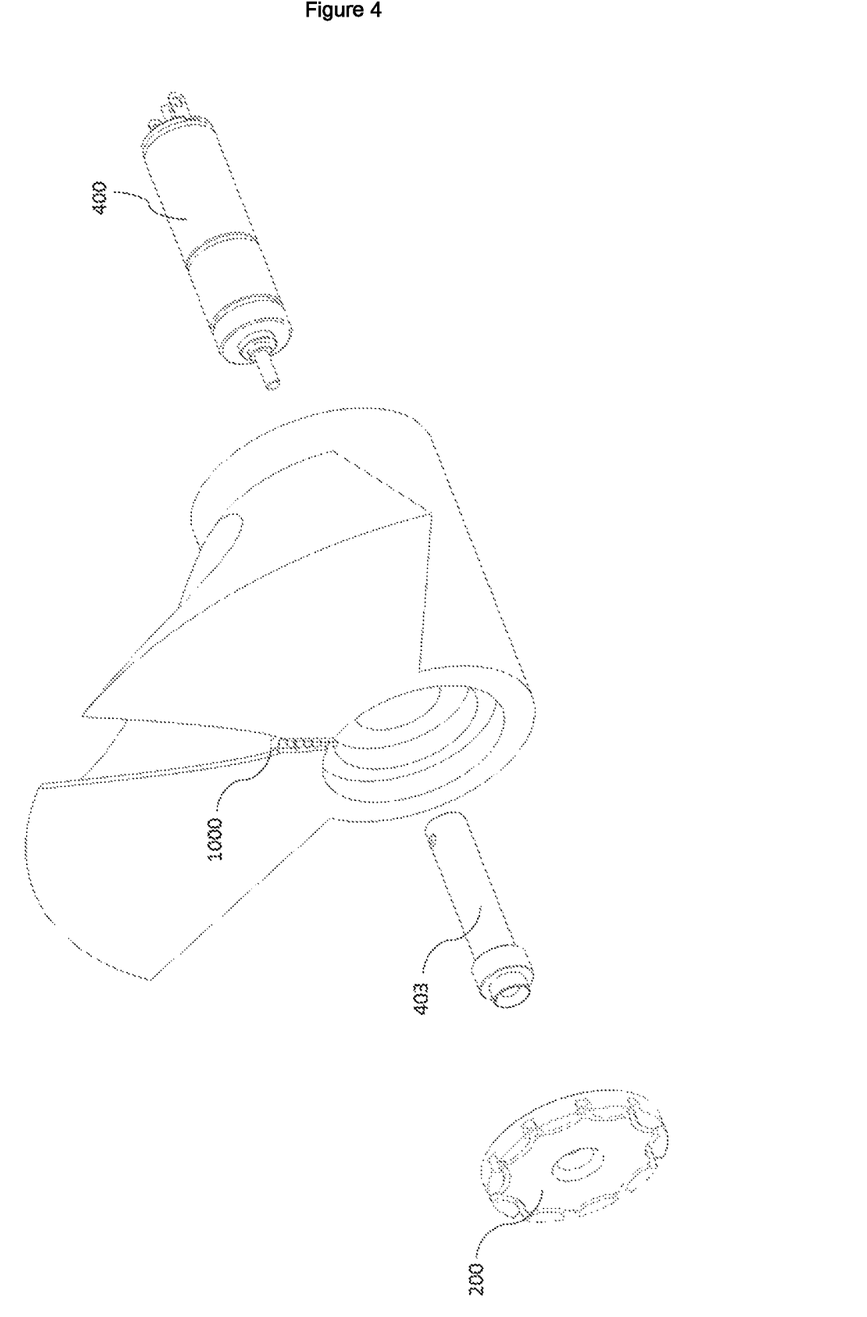
FIG. 4 shows an exploded view of the device's selecting portion according to the same embodiment shown in FIG. 3.

FIG. 3A shows an isometric view of an implemented embodiment of the device's selecting portion according to the invention. As shown in the Figure, the device comprises a channel 100 having a funnel-like proximal end 101 designed to facilitate the canalization of a plurality of biological entities 1000 into the channel body 102. The channel body 102 has a quasi-cylindrical appearance with a mean diameter of 2 mm and a round cross-section of the distal end 103 of 1.2 mm, which has been designed to easily accommodate and canalize zebrafish eggs or larvae dispersed into a liquid medium without experiencing any major pressure or capillarity drawback. The selector 200 is embodied as a gearwheel comprising a plurality of slots 201, in this embodiment fluidically connected among them via backchannels 202 located inwardly within the selector 200 to facilitate fluidic flows during sorting operations. A rotational actuator 400 is operatively connected to the gearwheel selector 200 via a gearbox 402 acting on a main axis 403 to operate rotation of the slots 201, as shown in a cross-sectional view in FIG. 3B. FIG. 4 shows an exploded view of the device's selecting portion according to the same embodiment.

Figure 5:
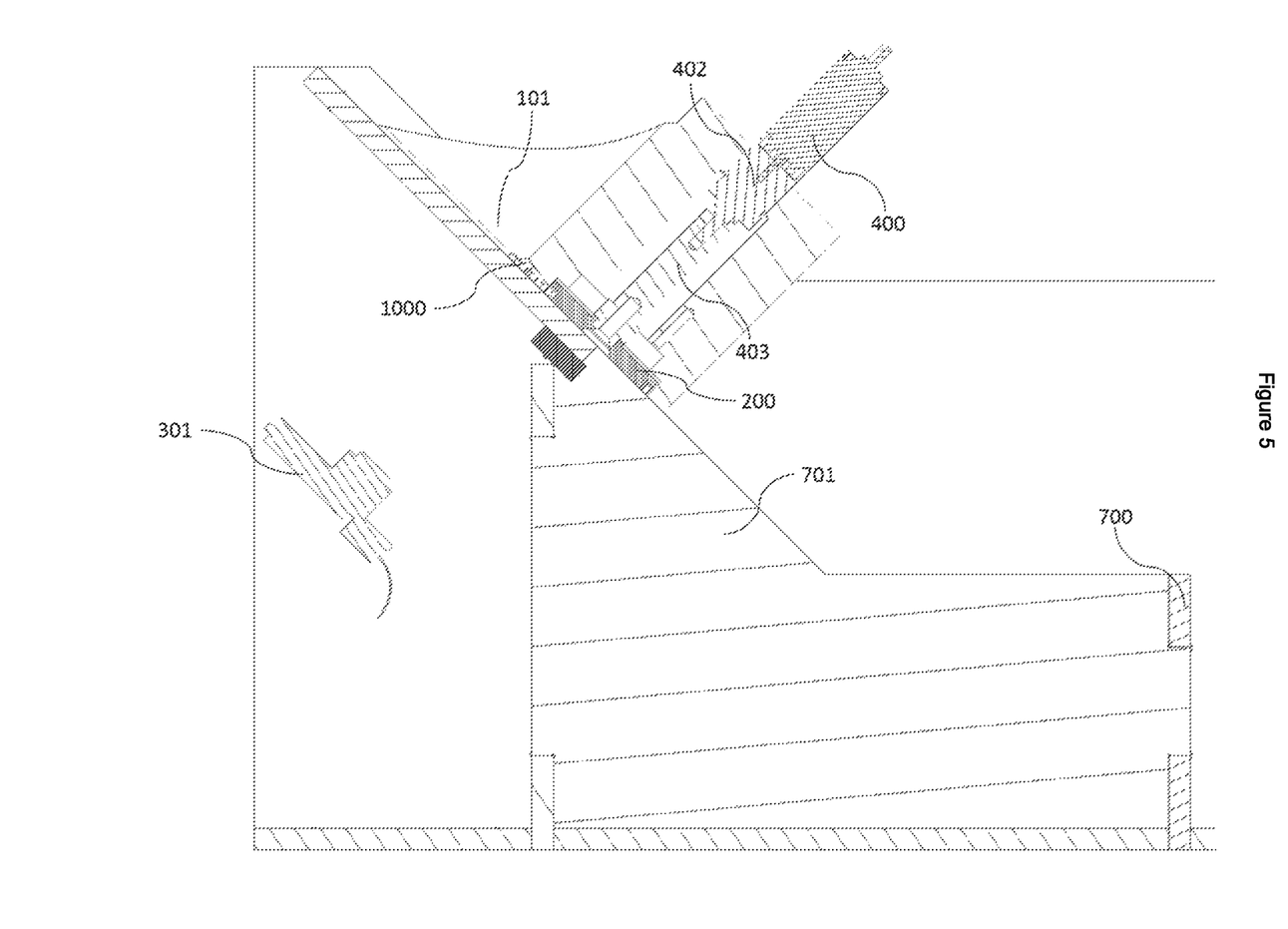
FIG. 5 depicts a sectional lateral view of the entire device according to one embodiment of the invention.
Figure 6:
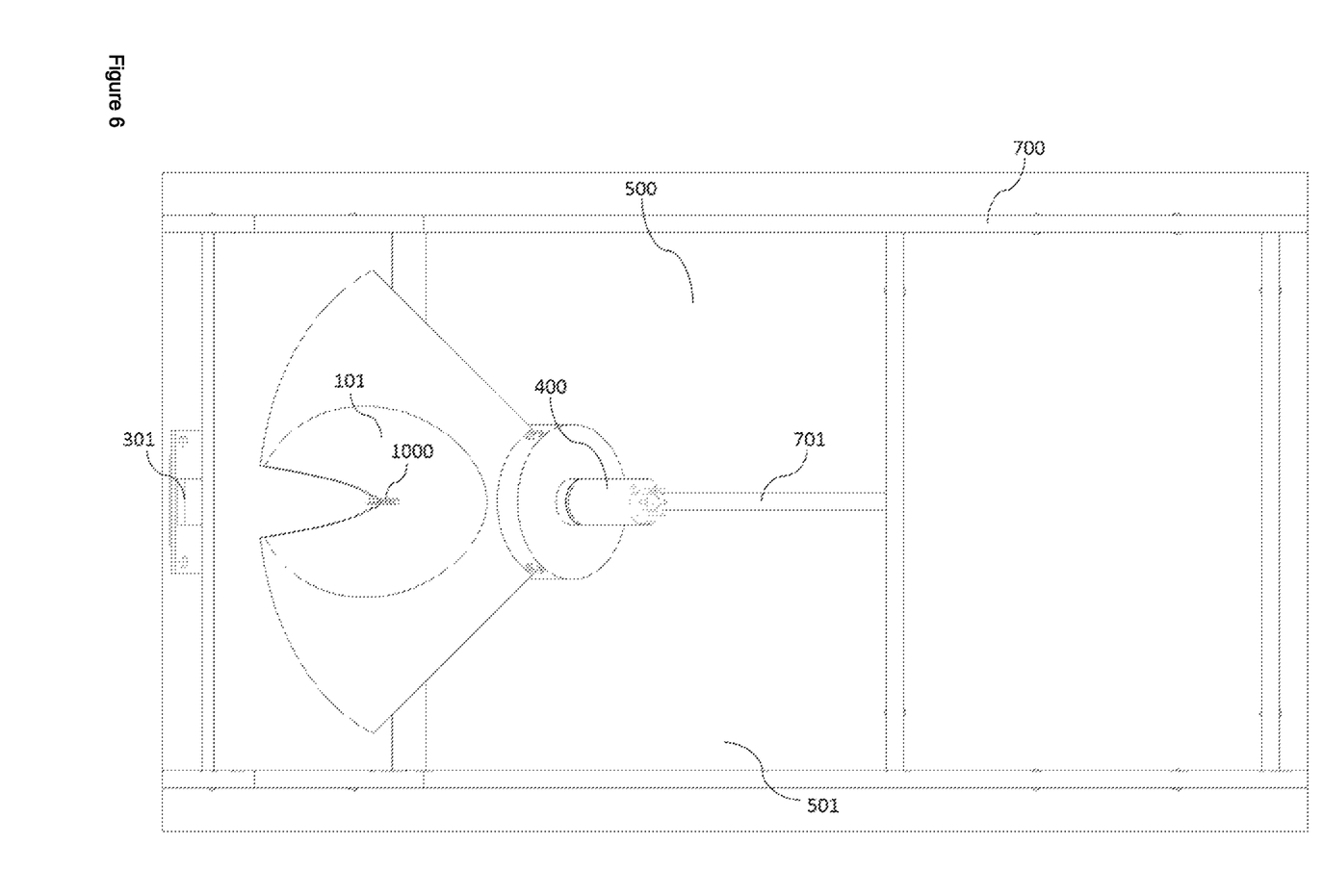
FIG. 6 shows a top view of the entire device according to the same embodiment shown in FIG. 5.

FIG. 5 depicts a sectional lateral view according to one embodiment of the invention. In the shown embodiment, the above-described selecting portion is located within a main frame 700 comprising two reservoirs 500 and 501 divided by a separator 701, as better shown in a top view of this embodiment of the device (FIG. 6). A camera 301 is located within the device so that its optical axis is parallel to the rotational axis of the actuator 400 and perpendicular to the channel's 100 longitudinal axis. The camera 301 is coupled with a computer device (not shown) so to form a system 300 for detecting and analysing an optical parameter of a biological entity 1000, said system acting on the selector 200 to sort said entities 1000. In a particular embodiment, the detecting and analysing system 300 comprising a camera 301 is adapted to operate the selector 200 on the basis of transparency of zebrafish larvae, so to sort fertilized from non-fertilized egg cells. In this way, fertilized egg cells can be dispensed into a dedicated reservoir 500 whereas non-fertilized egg cells could be eliminated from further analysis upon disposal into a waste reservoir 501.

As a way of example, after a zebrafish egg cell 1000 is located within a slot 201 of the selector 200, detection and analysis of the transparency of zebrafish egg cells 1000 is performed by a system 300 comprising a camera and a computer device. At this point, the selector 200 is in a rest position A. Based on the examination of a transparency threshold, the detection and analysis system 300 actuates the actuator 400 by inducing a clockwise or counter-clockwise turn of the selector 200, so that this latter can switch from the rest position A to a clockwise sorting positions A' or to a counter-clockwise sorting position A", the first allowing for the sorting of transparent (fertilized) zebrafish egg cells into the collection reservoir 500, and the second one allowing for the sorting of opaque (non-fertilized) zebrafish egg cells into a disposal reservoir 501.

The invention claimed is:

1. A device for mechanically sorting a solid biological entity based on an optical parameter of the biological entity, the device comprising:
a channel having a proximal end, a distal end, and an elongated body between the proximal end and the distal end, the proximal end configured to operatively connect with a reservoir that includes the biological entity;
an optical device configured to detect and analyze the optical parameter of the biological entity; and
a selector including at least one slot, the selector operatively connected with the distal end of the channel and with the optical device, the selector being shaped to accommodate the biological entity within one of the at least one slot,
wherein the selector is configured to switch from a rest position to a plurality of sorting positions based on a detection and analysis of the optical parameter of the biological entity, and
wherein the optical device is configured to detect and analyze the biological entity that is located inside the one of the at least one slot.

2. The device of claim 1, wherein the channel is configured for fluidic transportation of the biological entity in a solid form that is dispersed in a fluid medium.

3. The device of claim 1, wherein the biological entity includes an egg cell, a zygote, an embryo, a grain, a pollen, an animal tissue, a portion of animal tissue, or a larva.

4. The device of claim 1, wherein the channel has a diameter between 0.5 mm and 20 mm.

5. The device of claim 3, wherein the egg cell, the zygote, the embryo or the larva is derived from an insect, an amphibian or a fish.

6. The device of claim 1, wherein the optical device for detecting and analyzing the optical parameter of the biological entity includes an optical sensor and a light source.

7. The device of claim 1, wherein the optical parameter of the biological entity includes at least one of a transparency, a reflectance, a contour, a morphology, and/or fluorescence.

8. The device of claim 1, wherein the selector includes a gearwheel having the at least one slot, the at least one slot shaped to accommodate the biological entity.

9. The device of claim 8, wherein the optical device for detecting and analyzing the optical parameter of the biological entity includes an optical sensor and a light source, wherein an optical axis of the optical sensor is arranged to be in parallel to a rotational axis of the gearwheel.

10. The device of claim 1, further comprising:
a receiving reservoir in correspondence to each one of the plurality of sorting positions of the selector.

11. The device of claim 1, wherein the optical device further includes a computer device operatively connected to the selector, the computer device configured to
analyze the detected optical parameter, and
switch the selector from a rest position to one of the plurality of sorting positions based on the analysis of the optical parameter of the biological entity that is located inside the one of the at least one slot.

12. A robotic system comprising:
a sorting device for mechanically sorting a solid biological entity, the sorting device including,
a channel having a proximal end, a distal end, and an elongated body between the proximal end and the distal end, the proximal end configured to operatively connect with a reservoir that includes the biological entity,
an optical device configured to detect and analyze an optical parameter of the biological entity, and
a selector including at least one slot, the selector operatively connected with the distal end of the channel and with the optical device, the selector being shaped to accommodate the biological entity within one of the at least one slot, the selector is configured to switch from a rest position to a plurality of sorting positions based on a detection and analysis of the optical parameter of the biological entity, and the optical device is configured to detect and analyze the biological entity that is located inside the one slot; and
a robotic element configured to distribute the biological entity into a reservoir after sorting with the sorting device.

13. The system of claim 12, wherein the channel is configured for fluidic transportation of the biological entity in a solid form that is dispersed in a fluid medium.

14. The system of claim 12, wherein the optical device for detecting and analyzing the optical parameter of the biological entity includes an optical sensor and a light source.

15. The system of claim 12, wherein the sorting device further comprises:
a receiving reservoir in correspondence to each one of the plurality of sorting positions of the selector.

16. The system of claim 12, wherein the optical device further includes a computer device operatively connected to the selector, the computer device configured to
analyze the detected optical parameter, and
switch the selector from a rest position to one of the plurality of sorting positions based on the analysis of the optical parameter of the biological entity that is located inside the one of the at least one slot.

17. The system of claim 12, wherein the selector includes a gearwheel having the at least one slot, the at least one slot shaped to accommodate the biological entity.

18. The system of claim 17, wherein the optical device for detecting and analyzing the optical parameter of the biological entity includes an optical sensor and a light source, wherein an optical axis of the optical sensor is arranged to be in parallel to a rotational axis of the gearwheel.

* * * * *